| United States Patent [19]
Ramalingam et al.

[11] Patent Number: 4,731,474
[45] Date of Patent: Mar. 15, 1988

[54] NOVEL THERAPEUTIC COMPOUNDS USEFUL AS HYPOLIPIDEMIC AND HYPOCHOLESTEREMIC AGENTS

[75] Inventors: Thallapalli Ramalingam; Yadavalli V. D. Nageswar; Maddamsetty V. Rao; Pralhad B. Sattur; Gopalakrishna Thyagarajan, all of Andhra Pradesh, India

[73] Assignee: Council of Scientific and Industrial Research, New Delhi, India

[21] Appl. No.: 820,410

[22] Filed: Jan. 17, 1986

[51] Int. Cl.$^4$ ............................................. C07C 59/48
[52] U.S. Cl. ................................................... 562/471
[58] Field of Search .......................... 170/61; 562/471; 574/571

[56] References Cited

FOREIGN PATENT DOCUMENTS 216572 10/1984 Czechoslovakia .

*Primary Examiner*—Paul J. Killos
*Attorney, Agent, or Firm*—Ladas & Parry

[57] ABSTRACT

The present invention relates to novel therapeutic compounds useful as hypolipidemic and hypocholesteremic agents and to a process for the preparation of such compounds. More particularly, the present invention relates to novel alkali metal salts of substituted α-(3-pentadecylphenoxy)-isobutyric acid, which have never been reported in the prior art and which have now been synthesized for the first time, and to a process for the preparation thereof.

12 Claims, No Drawings

NOVEL THERAPEUTIC COMPOUNDS USEFUL AS HYPOLIPIDEMIC AND HYPOCHOLESTEREMIC AGENTS

The present invention provides novel alkali metal salts of substituted α-(3-pentadecylphenoxy)-isobutyric acid of the general formula:

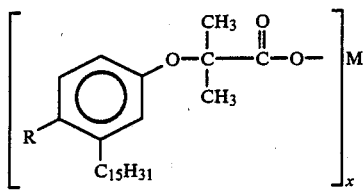

wherein R is hydrogen or halogen, M is an alkali metal and x is 1 or 2 depending on the nature of the alkali metal.

The preferred halogen substitute for R in the above-mentioned formula is chlorine while the preferred alkali metals denoted by M are sodium, magnesium and calcium.

The novel compounds of the present invention carry a long alkyl chain of $C_{15}$ carbon atoms in the meta position to the side chain. The compounds have been found to possess particularly beneficial therapeutic activity in the reduction of serum cholesterol and triglyceride levels in rodents and evince substantially little toxicity.

According to a further feature of the invention, the novel alkali metal salts of the general formula:

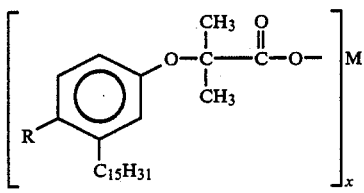

wherein R, M and x are as defined herein are prepared by a process which comprises reacting a correspondingly substituted α-(3-pentadecylphenoxy)-isobutyric acid of the general formula:

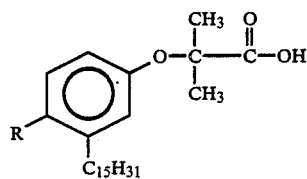

wherein R is as defined above with an alkali metal salt followed by recovery of the desired product.

Preferably, the reaction is carried out in the presence of an aqueous alcoholic medium wherein the alcohol is selected from aliphatic alcohols having from 1 to 5 carbon atoms. The pH of the reaction mixture is conveniently maintained at about 8.

The alkali metals whose salts are employed for the reaction are as identified above and the salts in question can include the hydroxides, carbonates and halides.

In the case of the sodium salt of α-(3-pentadecylphenoxy)-isobutyric acid, x in the general formula stated above is 1. In the case of the calcium and magnesium salts of this acid, x is 2.

In the examples that follow, the preparation of the sodium, magnesium and calcium salts of α-(3-pentadecylphenoxy)-isobutyric acid is described in greater detail. However, the sodium and magnesium salts have been found not to possess justifiable cholesterol and triglyceride reducing action. Hence, it is only the calcium salt of α-(3-pentadecylphenoxy)-isobutyric acid which has been investigated in detail and which possesses significant cholesterol and triglyceride reducing action in experimental animals.

The following examples describe non-limitatively the preparation of the novel compounds of the invention.

EXAMPLE 1

Sodium α-(3-pentadecylphenoxy)-isobutyrate 100 g α-(3-pentadecylphenoxy)-isobutyric acid were dissolved in 250 ml ethanol. To this ethanolic solution, 15 g sodium hydroxide were added dropwise and the entire reaction mixture was refluxed with stirring for about 30 minutes. The solvent was recovered and the residue was washed with acetone and dried.

The yield of the recovered product sodium α-(3-pentadecylphenoxy)-isobutyrate was 95% with the product having a melting point of from 89°–91° C.

EXAMPLE 2

Calcium α-(3-pentadecylphenoxy)-isobutyrate 100 g α-(3-pentadecylphenoxy)-isobutyric acid were dissolved in 250 ml ethanol. To this solution, 10 g aqueous sodium hydroxide in 60 ml water, were added until the pH of the reaction mixture was about 8.0. A solution of 35 g calcium chloride in 300 ml water was added dropwise with stirring and the separated white solid was filtered, washed with water and dried.

The yield of the recovered product calcium α-(3-pentadecylphenoxy)-isobutyrate was 98% with the product having a melting point of from 106° C. to 108° C.

EXAMPLE 3

Magnesium α-(3-pentadecylphenoxy)-isobutyrate 100 g α-(3-pentadecylphenoxy)-isobutyric acid were dissolved in 250 ml ethanol. To this solution, 10 g aqueous sodium hydroxide in 60 ml water were added until the pH of the reaction mixture was 8.0. A solution of 65 g magnesium sulphate in 500 ml water was added dropwise with stirring and the gummy white solid which separated out was filtered, washed with water and dried.

The yield of the gummy product identified as magnesium α-(3-pentadecylphenoxy)-isobutyrate was 94% which could not be purified.

In the further examples which follow, the hypolipidemic activity of different doses of the novel calcium salts of α-(3-pentadecylphenoxy)-isobutyric acid of the present invention when administered over varying periods of time is compared with the activity of a known hypolipidemic, viz. clofibrate, administered over similar periods.

EXAMPLE 4

HYPOLIPIDEMIC ACTIVITY OF CALCIUM SALT OF α-(3-PENTADECYLPHENOXY)-ISOBUTYRIC ACID AND CLOFIBRATE

4 DAYS TREATMENT

Rats of both sexes were divided into three groups. Group I served as control and was treated with vehicle, i.e. gum acacia or carboxymethyl cellulose, (1 ml/100 g body weight). Group II was treated with the calcium salt of α-(3-pentadecylphenoxy)-isobutyric acid (200 mg/kg body weight) and Group III was treated with clofibrate (200 mg/kg body weight). On the fifth day, all were sacrificed. Blood was collected by cardiac puncture under light ether anaesthesia and lipid profile in serum were studied. The results are expressed as mean±SE in Table I hereafter:

TABLE I

| LIPID PROFILE | GROUP I (n = 7) | GROUP II (n = 8) | GROUP III (n = 6) |
|---|---|---|---|
| Triglycerides mg % | 65.71 ± 2.02 | 56.25*** ± 2.23 | 43.33**** ± 1.67 |
| Serum Cholesterol | | | |
| Total mg % | 107.14 ± 1.84 | 75.62**** ± 2.20 | 72.50**** ± 2.14 |
| Esterified mg % | 63.57 ± 2.25 | 59.37* ± 1.48 | 60.00* ± 1.83 |
| Free mg % | 42.14 ± 2.14 | 16.25**** ± 1.83 | 12.50**** ± 1.12 |
| Total lipid mg % | 370.71 ± 4.24 | 356.87** ± 2.49 | 290.17**** ± 6.40 |
| Free fatty acids mEq/lit | 1.01 ± 0.02 | 0.93** ± 0.01 | 0.87**** ± 0.01 |
| Serum lipoproteins | | | |
| Alpha % | 39.86 ± 0.18 | 35.00** ± 1.74 | 38.67*** ± 0.18 |
| Beta % | 60.14 ± 0.18 | 65.00** ± 1.74 | 60.14* ± 0.18 |

Significance: Compared with control values
p values: *ns <0.05 *<0.01 ****<0.001
n: Number of animals used.

EXAMPLE 5

HYPOLIPIDEMIC ACTIVITY OF CALCIUM SALT OF α-(3-PENTADECYLPHENOXY)-ISOBUTYRIC ACID AND CLOFIBRATE

7 DAYS TREATMENT

Rats of either sex were divided into 3 groups. Group I served as control and were treated with vehicle (1 ml/100 g body weight). Group II was treated with calcium salt of α-(3-pentadecylphenoxy)-isobutyric acid (200 mg/kg p.o.) and group III was treated with clofibrate (200 mg/kg body weight). On the eighth day, the rats were sacrificed and blood was collected by cardiac puncture under light ether anaesthesia. The lipid profile was studied and the results are expressed as mean±SE in Table II hereafter:

TABLE II

| LIPID PROFILE | GROUP I (n = 7) | GROUP II (n = 6) | GROUP III (n = 6) |
|---|---|---|---|
| Triglycerides mg % | 65.71 ± 2.97 | 28.33**** ± 2.79 | 30.83**** ± 1.54 |
| Serum Cholesterol | | | |
| Total | 105.00 ± 2.44 | 75.00**** ± 2.58 | 80.83**** ± 2.39 |
| Esterified | 63.57 ± 1.43 | 57.50* ± 2.39 | 65.83* ± 1.54 |
| Free | 41.43 ± 2.10 | 17.50**** ± 2.01 | 15.00**** ± 1.83 |
| Total lipid mg % | 389.28 ± 11.63 | 301.33**** ± 5.07 | 342.83**** ± 8.70 |
| Free fatty acid mEq/lit | 1.027 ± 0.03 | 0.89**** ± 0.02 | 0.82**** ± 0.01 |
| Serum lipoproteins | | | |
| Alpha % | 40.00 ± 0.17 | 39.33* ± 2.56 | 39.84* ± 0.31 |
| Beta % | 60.00 ± 0.17 | 62.67* ± 2.56 | 60.16* ± 0.31 |

Significance: Compared with control values
p values: *ns <0.05 *<0.01 ****<0.001
n: Number of animals used

EXAMPLE 6

HYPOLIPIDEMIC ACTIVITY OF DIFFERENT DOSES OF CALCIUM SALT OF α-(3-PENTADECYLPHENOXY)-ISOBUTYRIC ACID

7 DAYS TREATMENT

Rats of either sex were divided into four groups. Group I served as control and were treated with vehicle (1 ml/100 g body weight). Groups II, III and IV were treated with calcium salt of α-(3-pentadecylphenoxy)-isobutyric acid with doses of 100 mg/kg, 200 mg/kg and 400 mg/kg orally, respectively. On the eighth day all were sacrificed and blood was collected by cardiac puncture under light ether anaesthesia. The lipid profile was studied and the results are expressed as mean±SE in Table III hereafter:

TABLE III

| LIPID PROFILE | GROUP I (n = 7) | GROUP II (n = 6) | GROUP III (n = 6) | GROUP IV (n = 6) |
|---|---|---|---|---|
| Triglycerides mg % | 65.71 ± 2.97 | 64.16* ± 1.54 | 28.33**** ± 2.79 | 30.83**** ± 2.39 |
| Serum Cholesterol | | | | |
| Total mg % | 105.00 ± 2.44 | 92.50** ± 2.50 | 75.00**** ± 2.58 | 65.00**** ± 1.29 |
| Esterified mg % | 63.57 ± 1.43 | 63.34* ± 2.19 | 57.50* ± 2.39 | 57.50*** ± 1.12 |

TABLE III-continued

| LIPID PROFILE | GROUP I (n = 7) | GROUP II (n = 6) | GROUP III (n = 6) | GROUP IV (n = 6) |
|---|---|---|---|---|
| Free mg % | 41.43 ± 2.10 | 29.16*** ± 1.70 | 17.50**** ± 2.01 | 7.50**** ± 1.12 |
| Total lipid mg % | 389.28 ± 11.63 | 367.33* ± 0.91 | 301.33**** ± 5.07 | 218.50**** ± 4.23 |
| Free fatty acids mEq/lit | 1.03 ± 0.03 | 1.01* ± 0.01 | 0.89**** ± 0.02 | 0.79**** ± 0.01 |
| Serum lipoproteins | | | | |
| Alpha % | 40.00 ± 0.17 | 38.17* ± 1.70 | 39.33* ± 2.56 | 32.83**** ± 0.87 |
| Beta % | 60.00 ± 0.17 | 61.50* ± 1.98 | 60.67* ± 2.56 | 67.17**** ± 0.87 |

Significance: Compared with control values
p values: *ns <0.05 *<0.01 ****<0.001
n: Number of animals used.

EXAMPLE 7

HYPOLIPIDEMIC ACTIVITY OF CALCIUM SALT OF α-(3-PENTADECYLPHENOXY)-ISOBUTYRIC ACID AND CLOFIBRATE

15 DAYS TREATMENT

Rats of either sex were divided into three groups. Group I served as control and were treated with vehicle (1 ml/100 g body weight). Group II was treated with calcium salt of α-(3-pentadecylphenoxy)-isobutyric acid (dose 200 mg/kg p.o.) and Group III was treated with clofibrate (200 mg/kg p.o.). On the sixteenth day the rats were sacrificed and blood was collected by cardiac puncture under light ether anaesthesia. The lipid profile was studied and the results are expressed as mean±SE in Table IV hereafter:

TABLE IV

| LIPID PROFILE | GROUP I (n = 7) | GROUP II (n = 0) | GROUP III (n = 6) |
|---|---|---|---|
| Triglycerides mg % | 64.28 ± 2.97 | 21.25**** ± 2.63 | 23.33**** ± 1.05 |
| Serum Cholesterol | | | |
| Total mg % | 105.71 ± 2.02 | 65.62**** ± 1.99 | 62.50**** ± 1.12 |
| Esterified mg % | 62.86 ± 1.01 | 53.12**** ± 1.88 | 53.33*** ± 2.11 |
| Free mg % | 42.86 ± 2.41 | 11.25**** ± 1.83 | 9.17**** ± 1.54 |
| Total lipid mg % | 383.29 ± 11.11 | 251.25**** ± 6.11 | 251.67**** ± 4.01 |
| Free fatty acids mEq/lit | 1.03 ± 0.04 | 0.83**** ± 0.01 | 0.79**** ± 0.004 |
| Serum lipoproteins | | | |
| Alpha % | 39.00 ± 0.69 | 30.37**** ± 1.02 | 35.50**** ± 0.22 |
| Beta % | 61.00 ± 0.69 | 69.63**** ± 1.02 | 64.50**** ± 0.22 |

Significance: Compared with control values
p values: *ns <0.05 *<0.01 ****<0.001
n: Number of animals used.

EXAMPLE 8

HYPOLIPIDEMIC ACTIVITY OF CALCIUM SALT OF α-(3-PENTADECYLPHENOXY)-ISOBUTYRIC ACID AND CLOFIBRATE

30 DAYS TREATMENT

Rats of either sex were divided into three groups. Group I served as control and received 1 ml of vehicle per 100 g body weight. Group II was treated with 200 mg/kg p.o. of calcium salt α-(3-pentadecylphenoxy)-isobutyric acid and Group III was treated with clofibrate 200 mg/kg p.o. On the thirty first day all were sacrificed and blood was collected by cardiac puncture under light ether anaesthesia. The lipid profile of serum was studied and the results are expressed as mean±SE in Table V hereafter:

TABLE V

| LIPID PROFILE | GROUP I (n = 7) | GROUP II (n = 7) | GROUP III (n = 6) |
|---|---|---|---|
| Triglycerides mg % | 66.43 ± 2.61 | 22.86**** ± 1.01 | 21.67**** ± 1.05 |
| Serum Cholesterol | | | |
| Total mg % | 101.43 ± 1.80 | 60.71**** ± 2.54 | 59.17**** ± 1.54 |
| Esterified mg % | 60.71 ± 2.54 | 50.71*** ± 1.30 | 51.67** ± 1.67 |
| Free mg % | 42.14 ± 1.01 | 7.14**** ± 1.01 | 7.50**** ± 1.12 |
| Total lipids mg % | 372.57 ± 4.30 | 234.28**** ± 5.17 | 226.67**** ± 3.33 |
| Free fatty acids mEq/lit | 0.993 ± 0.04 | 0.76**** ± 0.01 | 0.75**** ± 0.004 |
| Serum lipoproteins | | | |
| Alpha % | 38.29 ± 1.78 | 28.57**** ± 1.43 | 33.17** ± 0.87 |
| Beta % | 61.71 ± 1.78 | 71.43*** ± 1.43 | 66.83** ± 0.87 |

Significance: Compared with control values
p values: *ns <0.05 *<0.01 ****<0.001
n: Number of animals used.

We claim:

1. Alkali metal salts of substituted α-(3-pentadecylphenoxy)-isobutyric acid of the general formula:

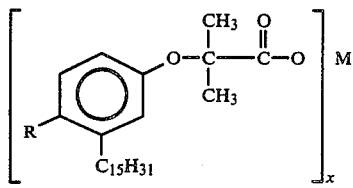

wherein R is a halogen, M is an alkali metal and x is 1 or 2.

2. A method for decreasing blood lipids comprising administering to a patient in need of a hypolipidemic, an effective amount of a composition comprising alkali metal salts of substituted α-(3-pentadecylphenoxy)-isobutyric acid of the general formula:

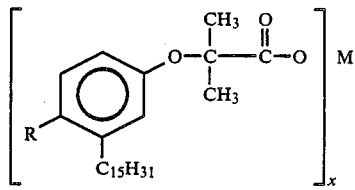

wherein R is hydrogen or halogen, M is an alkali metal and x is 1 or 2, and a pharmaceutically acceptable vehicle.

3. A method, as in claim 2, wherein said alkali metal salt of substituted α-(3-pentadecylphenoxy)isobutyl acid comprises sodium α-(3-pentadecylphenoxy)-isobutyrate.

4. A method, as in claim 2, wherein said alkali metal salt of substituted α-(3-pentadecylphenoxy)isobutyl acid comprises magnesium α-(3-pentadecylphenoxy)-isobutyrate.

5. A method, as in claim 2, wherein said blood lipids comprise cholesterol and triglycerides.

6. A method, as in claim 2, wherein said effective amount comprises 200 mg/kg of body weight.

7. A method, as in claim 5, wherein M is calcium and x=2.

8. A method, as in claim 7, wherein R is a halogen.

9. A method, as in claim 7, wherein R is chlorine.

10. A compound, as in claim 1, wherein R is chlorine.

11. A compound, as in claim 1, wherein M is calcium and x=2.

12. A compound, as in claim 1, wherein M is calcium.

* * * * *